(12) United States Patent
DeLucas

(10) Patent No.: US 7,247,490 B2
(45) Date of Patent: Jul. 24, 2007

(54) METHOD FOR SCREENING CRYSTALLIZATION CONDITIONS IN SOLUTION CRYSTAL GROWTH

(75) Inventor: Lawrence James DeLucas, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 742 days.

(21) Appl. No.: 10/161,141

(22) Filed: May 30, 2002

(65) Prior Publication Data

US 2003/0022384 A1    Jan. 30, 2003

Related U.S. Application Data

(63) Continuation of application No. 09/543,326, filed on Apr. 5, 2000, now abandoned.

(60) Provisional application No. 60/128,018, filed on Apr. 6, 1999.

(51) Int. Cl.
*G01N 33/00* (2006.01)

(52) U.S. Cl. ............................................. 436/86

(58) Field of Classification Search ............... 436/86
See application file for complete search history.

(56) References Cited

U.S. PATENT DOCUMENTS

| | | |
|---|---|---|
| 3,570,515 A | 3/1971 | Kinner |
| 3,747,628 A | 7/1973 | Holster et al. |
| 4,046,159 A | 9/1977 | Pegourie |
| 4,119,368 A | 10/1978 | Yamazaki |
| 4,153,855 A | 5/1979 | Feingold |
| 4,245,673 A | 1/1981 | Bouteille et al. |
| 4,263,010 A | 4/1981 | Randolph |
| 4,434,704 A | 3/1984 | Surjaatmadja |
| 4,517,048 A | 5/1985 | Shlichta |
| 4,668,584 A | 5/1987 | Uzgiris et al. |
| 4,755,363 A | 7/1988 | Fujita et al. |
| 4,833,233 A | 5/1989 | Carter |
| 4,886,646 A | 12/1989 | Carter et al. |
| 4,898,582 A | 2/1990 | Faste |
| 4,900,147 A | 2/1990 | Bowley et al. |
| 4,909,933 A | 3/1990 | Carter et al. |
| 4,919,899 A | 4/1990 | Herrmann et al. |
| 4,948,564 A | 8/1990 | Lyman et al. |
| 5,009,861 A | 4/1991 | Plaas-Link |

(Continued)

FOREIGN PATENT DOCUMENTS

AU            779792              6/2005

(Continued)

OTHER PUBLICATIONS

"RAMC 1999—Round Table Notes," particularly regarding Robotics (starting at bottom of 1st page), printed from http://www.hamptonresearch.com/stuff/RAMC99TRN.html.com on Aug. 21, 2002 (7 pages).

(Continued)

*Primary Examiner*—Monique T. Cole
(74) *Attorney, Agent, or Firm*—Bingham McCutchen LLP

(57) ABSTRACT

A method of screening protein crystal growth conditions with picogram to microgram amounts of protein in picoliter or nanoliter volumes is provided. A preferred method comprises a microarray with a plurality of micro-chambers in the microarray. A protein solution is placed into the micro-chambers by an automated dispensing mechanism. The protein crystal growth conditions of each of the micro-chambers is adjusted so that the protein crystal growth conditions in at least two of the micro-chambers differs. Crystallization of the protein solution in the micro-chambers is effected. Protein crystal growth in the micro-chambers is then observed.

2 Claims, 4 Drawing Sheets

U.S. PATENT DOCUMENTS

| | | | |
|---|---|---|---|
| 5,013,531 A | 5/1991 | Snyder et al. |
| 5,076,698 A | 12/1991 | Smith et al. |
| 5,078,975 A | 1/1992 | Rhodes et al. |
| 5,085,562 A | 2/1992 | Van Lintel |
| 5,088,515 A | 2/1992 | Kamen |
| 5,096,388 A | 3/1992 | Weinberg |
| 5,096,676 A | 3/1992 | McPherson et al. |
| 5,106,592 A | 4/1992 | Stapelmann et al. |
| 5,124,935 A | 6/1992 | Wallner et al. |
| 5,126,115 A | 6/1992 | Fujita et al. |
| 5,130,105 A | 7/1992 | Carter et al. |
| 5,164,558 A | 11/1992 | Huff et al. |
| 5,171,132 A | 12/1992 | Miyazaki et al. |
| 5,193,685 A | 3/1993 | Trevithick |
| 5,221,410 A | 6/1993 | Kushner et al. |
| 5,224,843 A | 7/1993 | Van Lintel |
| 5,256,241 A | 10/1993 | Noever |
| 5,259,737 A | 11/1993 | Kamisuki et al. |
| 5,265,327 A | 11/1993 | Faris et al. |
| 5,290,240 A | 3/1994 | Horres, Jr. |
| 5,336,062 A | 8/1994 | Richter |
| 5,346,372 A | 9/1994 | Naruse et al. |
| 5,362,325 A | 11/1994 | Shiraishi et al. |
| 5,375,979 A | 12/1994 | Trah |
| 5,376,252 A | 12/1994 | Ekstrom et al. |
| 5,400,741 A | 3/1995 | DeTitta et al. |
| 5,419,278 A | 5/1995 | Carter |
| 5,423,287 A | 6/1995 | Usami et al. |
| 5,529,465 A | 6/1996 | Zengerle et al. |
| 5,531,185 A | 7/1996 | Asano et al. |
| 5,544,254 A | 8/1996 | Hartley et al. |
| 5,581,476 A | 12/1996 | Osslund |
| 5,593,130 A | 1/1997 | Hansson et al. |
| 5,637,469 A | 6/1997 | Wilding et al. |
| 5,641,681 A | 6/1997 | Carter |
| 5,642,015 A | 6/1997 | Whitehead et al. |
| 5,643,540 A | 7/1997 | Carter et al. |
| 5,659,171 A | 8/1997 | Young et al. |
| 5,660,370 A | 8/1997 | Webster |
| 5,681,024 A | 10/1997 | Lisec et al. |
| 5,705,018 A | 1/1998 | Hartley |
| 5,716,852 A | 2/1998 | Yager et al. |
| 5,726,404 A | 3/1998 | Brody et al. |
| 5,728,559 A | 3/1998 | Nilsson et al. |
| 5,759,014 A | 6/1998 | Van Lintel |
| 5,775,371 A | 7/1998 | Pan et al. |
| 5,790,421 A | 8/1998 | Osslund |
| 5,836,750 A | 11/1998 | Cabuz |
| 5,842,787 A | 12/1998 | Kopf-Sill et al. |
| 5,855,753 A | 1/1999 | Trau et al. |
| 5,869,604 A | 2/1999 | Rousseau et al. |
| 5,872,010 A | 2/1999 | Karger et al. |
| 5,873,394 A | 2/1999 | Meltzer |
| 5,875,817 A | 3/1999 | Carter |
| 5,876,187 A | 3/1999 | Afromowitz et al. |
| 5,876,675 A | 3/1999 | Kennedy |
| 5,885,470 A | 3/1999 | Parce et al. |
| 5,922,210 A | 7/1999 | Brody et al. |
| 5,932,100 A | 8/1999 | Yager et al. |
| 5,932,799 A | 8/1999 | Moles |
| 5,942,443 A | 8/1999 | Parce et al. |
| 5,948,684 A | 9/1999 | Weigl et al. |
| 5,958,694 A | 9/1999 | Nikiforov |
| 5,961,934 A | 10/1999 | Arnowitz et al. |
| 5,964,995 A | 10/1999 | Nikiforov et al. |
| 5,971,158 A | 10/1999 | Yager et al. |
| 5,973,779 A | 10/1999 | Ansari et al. |
| 5,974,867 A | 11/1999 | Forster et al. |
| 5,985,356 A | 11/1999 | Schultz et al. |
| 5,997,636 A | 12/1999 | Gamarnik et al. |
| 6,007,309 A | 12/1999 | Hartley |
| 6,007,775 A | 12/1999 | Yager et al. |
| 6,031,082 A | 2/2000 | Nielsson et al. |
| 6,036,920 A | 3/2000 | Pantoliano et al. |
| 6,039,804 A | 3/2000 | Kim et al. |
| 6,043,080 A | 3/2000 | Lipshutz et al. |
| 6,057,159 A | 5/2000 | Lepre |
| 6,069,934 A | 5/2000 | Verman et al. |
| 6,110,273 A | 8/2000 | Sanjoh |
| 6,110,986 A | 8/2000 | Nozawa et al. |
| 6,117,232 A | 9/2000 | Sanjoh |
| 6,123,769 A | 9/2000 | Sanjoh |
| 6,129,826 A | 10/2000 | Nikiforov et al. |
| 6,134,950 A | 10/2000 | Forster et al. |
| 6,136,272 A | 10/2000 | Weigl et al. |
| 6,143,248 A | 11/2000 | Kellogg et al. |
| 6,155,282 A | 12/2000 | Zachary et al. |
| 6,156,181 A | 12/2000 | Parce et al. |
| 6,171,865 B1 | 1/2001 | Weigl et al. |
| 6,174,365 B1 | 1/2001 | Sanjoh |
| 6,174,675 B1 | 1/2001 | Chow et al. |
| 6,186,660 B1 | 2/2001 | Kopf-Sill et al. |
| 6,235,175 B1 | 5/2001 | Dubrow et al. |
| 6,238,538 B1 | 5/2001 | Parce et al. |
| 6,258,331 B1 | 7/2001 | Sanjoh |
| 6,268,158 B1 | 7/2001 | Pantoliano et al. |
| 6,291,192 B1 | 9/2001 | Pantoliano et al. |
| 6,296,673 B1 | 10/2001 | Santarsiero et al. |
| 6,296,811 B1 | 10/2001 | Sasaki |
| 6,297,021 B1 | 10/2001 | Nienaber et al. |
| 6,303,322 B1 | 10/2001 | Pantoliano et al. |
| 6,319,315 B1 | 11/2001 | Sanjoh |
| 6,368,402 B2 | 4/2002 | DeTitta et al. |
| 6,387,273 B1 | 5/2002 | Abedi |
| 6,402,837 B1 | 6/2002 | Shtrahman et al. |
| 6,404,849 B1 | 6/2002 | Olson et al. |
| 6,406,903 B2 | 6/2002 | Bray et al. |
| 6,409,832 B2 | 6/2002 | Weigl et al. |
| 6,413,778 B1 | 7/2002 | Carpenter et al. |
| 6,417,007 B1 | 7/2002 | Gittleman et al. |
| 6,423,536 B1 | 7/2002 | Jovanovich et al. |
| 6,454,945 B1 | 9/2002 | Weigl et al. |
| 6,468,346 B2 | 10/2002 | Arnowitz et al. |
| 6,488,896 B2 | 12/2002 | Weigl et al. |
| 6,630,006 B2 | 10/2003 | Santarsiero et al. |
| 6,719,840 B2 * | 4/2004 | David et al. ................. 117/68 |
| 6,742,661 B1 | 6/2004 | Schulte et al. |
| 6,743,399 B1 | 6/2004 | Weigl et al. |
| 2001/0016191 A1 | 8/2001 | Osslund |
| 2001/0016314 A1 | 8/2001 | Anderson et al. |
| 2001/0019845 A1 | 9/2001 | Bienert et al. |
| 2001/0027745 A1 | 10/2001 | Weigl et al. |
| 2001/0032582 A1 | 10/2001 | DeTitta et al. |
| 2001/0055669 A1 | 12/2001 | Schultz et al. |
| 2001/0055775 A1 | 12/2001 | Schultz et al. |
| 2002/0022250 A1 | 2/2002 | Hendrickson et al. |
| 2002/0029814 A1 | 3/2002 | Unger et al. |
| 2002/0048610 A1 | 4/2002 | Cima et al. |
| 2002/0054663 A1 | 5/2002 | Olson et al. |
| 2002/0062783 A1 | 5/2002 | Bray |
| 2002/0064485 A1 | 5/2002 | Delucas et al. |
| 2002/0067800 A1 | 6/2002 | Newman et al. |
| 2002/0164812 A1 | 11/2002 | DeLucas et al. |
| 2003/0022383 A1 | 1/2003 | DeLucas |
| 2003/0022384 A1 | 1/2003 | DeLucas et al. |
| 2003/0027348 A1 | 2/2003 | DeLucas et al. |
| 2003/0096421 A1 | 5/2003 | DeLucas et al. |
| 2003/0180960 A1 | 9/2003 | Consenza et al. |

FOREIGN PATENT DOCUMENTS

| | | |
|---|---|---|
| DE | 19631395 | 2/1998 |
| EP | 0 553539 A1 | 8/1993 |
| EP | 592 094 | 4/1994 |

| | | |
|---|---|---|
| EP | 703 364 | 3/1996 |
| EP | 706 004 | 4/1996 |
| EP | 779 436 | 6/1997 |
| EP | 0 815 940 | 1/1998 |
| EP | 829 360 | 3/1998 |
| EP | 845 603 | 6/1998 |
| EP | 999 055 | 10/2000 |
| GB | 2 155 152 | 9/1985 |
| GB | 2 308 460 | 6/1997 |
| JP | 02001013054 A | 1/2001 |
| WO | WO 98/07069 | 2/1998 |
| WO | WO 99/00655 | 1/1999 |
| WO | WO 99/04361 | 1/1999 |
| WO | WO 99/17093 | 4/1999 |
| WO | WO 99/23284 | 5/1999 |
| WO | WO 99/52633 | 10/1999 |
| WO | WO 00/00678 | 1/2000 |
| WO | WO 00/43748 | 7/2000 |
| WO | WO 00/60345 | 10/2000 |
| WO | WO 00/60345 A1 | 10/2000 |
| WO | WO 00/78445 | 12/2000 |
| WO | WO 01/09595 | 2/2001 |
| WO | WO 01/26797 A2 | 4/2001 |
| WO | WO 01/92293 A2 | 12/2001 |
| WO | WO 03/012430 | 2/2003 |

OTHER PUBLICATIONS

Abbott, "Structures by numbers," Nature 408:130-132 (Nov. 9, 2000).

Baird, J.K., "Theory of protein crystal nucleation and growth controlled by solvent evaporation," J. Cryst. Growth 204:553-562 (1999).

Baldock, P. et al., "A comparison of microbatch and vapour diffusion for initial screening of crystallization conditions," J. Cryst. Growth 168:170-174 (1996).

Beckmann, W. et al., "The Effect of Additives on Nucleation: A Low Cost Automated Apparatus," J. Crystal Growth 99:1061-1064 (1990).

Berry, M.B., "Protein Crystallization: Theory and Practice," excerpts from "Structure and Dynamics of E. coli Adenylate Kinase," by Michael B. Berry (Sep. 17, 1995), 12 pages, printed from http://www.bioc.nce.edu/~berry/crystallization/crystallization.

Blow, D.M. et al., "Control of nucleation of protein crystals," Protein Sci. 3:1638-1643 (1994).

Brodersen, D.E. et al., "Computer Programs—XAcr : a program for construction, automated setup and bookkeeping of crystallization experiments," J. Appl. Cryst. 32:1012-1016 (1999).

Bullock, E. et al., "Apparatus for the growth of crystals from small volumes of solution," J. Physics E: Sci. Instrum. 5:412-413 (1972).

Burley, S. K. et al., "Structural genomics: beyond the Human Genome Project," Nat. Genet. 23:151-157 (1999).

Carter, C.W., "Efficient Factorial Designs and the Analysis of Macromolecular Crystal Growth Conditions," Methods: A Companion to Meth. Enzymol. 1(1):12-24 (1990).

Casay, G.A. et al., "Laser scattering in a hanging drop vapor diffusion apparatus for protein crystal growth in a microgravity environment," J. Crystal Growth 122:95-101 (1992).

Chayen, N.E., "A novel technique to control the rate of vapour diffusion, giving larger protein crystals," J. Appl. Cryst. 30:198-202 (1997).

Chayen, N.E., "Comparative studies of Protein Crystallization by Vapour-Diffusion and Microbatch Techniques," Acta Cryst. D54:8-15 (1998).

Chayen, N.E., "Protocol: A novel technique for containerless protein crystallization," Protein Engineering 9(10):927-929 (1990).

Chayen, N.E., "Tackling the bottleneck of protein crystallization in the post-genomic era," Trends Biotech. 20(3):98 (2002).

Chayen, N.E., "The role of oil in macromolecular crystallization," Structure 5(10):1269-1274 (1997).

Chayen, N.E. et al., "An Automated System for Micro-Batch Protein Crystallization and Screening," J. Appl. Cryst. 23:297-302 (1990).

Chayen, N.E. et al., "Apocrustacyanin A1 from the lobster carotenoprotein a-crustacyanin: crystallization and inital X-ray analysis involving softer X-rays," Acta Cryst. D56:1064-1066 (Aug. 2000).

Chayen, N.E. et al., "Control of nucleation in the crystallization of lysozyme," Protein Sci. 2:113-118 (1993).

Chayen, N.E. et al., "Microbatch crystallization under oil—a new technique allowing many small-volume crystallization trials," J. Crystal Growth 122:176-180 (1992).

Chayen, N.E., et al., "New developments of the IMPAX small-volume automated crystallization system," Acta Cryst. D50:456-458 (1994).

Chayen, N.E. et al., "Porous Silicon: an Effective Nucleation-inducing Material for Protein Crystallization," J. Mol. Biol. 312:591-595 (2001).

Chayen, N.E. et al., "Protein crystallization for genomics: towards high-throughput optimization techniques," Acta Cryst. D58:921-927 (2002).

Chayen, N.E. et al., "Purification, crystallization and initial X-ray analysis of the $C_1$ subunit of the astaxanthin protein, $V_{600}$, of the chondrophore Velella velella," Acta Cryst. D55:266-268 (1999).

Chayen, N.E. et al., "Space-grown crystals may prove their worth," Nature 398(6722):20 (1990).

Chayen, N.E. et al., "Trends and Challenges in Experimental Macromolecular Crystallography," Quart. Rev. Biophysics 29(3):227-278 (Aug. 1996).

Cianci, M. et al., "Structure of lobster apocrustacyanin $A_1$ using softer X-rays," Acta Cryst. D57:1219-1229 (Apr. 2001).

Cox, M. J. et al., "An Investigation of Protein Crystallization Parameters using Successive Automated Grid Searches (SAGS)," J. Cryst. Growth 90(1-3):318-324 (1988).

Cox, M.J. et al., "Experiments with Automated Protein Crystallization," J. Appl. Cryst. 20:366-373 (1987).

Cudney, B. et al., "Screening and Optimization Strategies for Macromolecular Crystal Growth," Acta Cryst. D50:414-423 (1994).

D'Arcy, A., "Crystallizing Proteins—a Rational Approach?," Acta Cryst. D50:469-471 (1994).

DeLucas et al., "New High-throughput Crystallization Technology," (Abstract E0014 from ACA2002 Meeting), printed from http://www.hwi.buffalo.edu/ACA on Apr. 10, 2002 (1 page).

Diller, D.J. et al., "An accurate numerical model for calculating the equilibration rate of a hanging-drop experiment," Acta Cryst. D55:656-663 (1999).

Dong, J. et al., "Bound-solvent structures for microgravity-, ground control-, gel- and microbatch-grown hen egg-white lysozyme crystals at 1.8 Å resolution," Acta Cryst. D55:745-752 (Apr. 1999).

Evans, P.R. et al., "Crystallographic Structure of Allosterically Inhibited Phosphofructokinase at 7Å Resolution," J. Mol. Biol. 191:713-720 (1986).

Fiehn, H. et al., "Microsystem Technology for Pipetting Systems: Parallel Sample Treatment in the Submicroliter Range (25),"  smallTalk2000 Association for Laboratory Automation Final Conference Program, San Diego, CA, held Jul. 8-12, 2000 (Abstract) (1 page).

Gaasterland, T., "Feasibility of Structural Genomics and Impact on Computational Biology: Post-Workshop Review," Mathematics and Computer Science Division, Argonne National Laboratory, Jan. 26, 1998 printed from http://www-fp.mcs.anl.gov/ ~gaasterland/sg-review. html on Apr. 12, 2002 (7 pages).

Gaasterland, T., "Structural genomics: Bioinformatics in the driver's seat," Nat. Biotech. 16:625-627 (Jul. 1998).

Gilliland, G. L. et al., "Screening For Crystallization Conditions and Robotics: Biological Macromolecule Crystallization Database, Version 3.0: New Features, Data and the NASA Archive for Protein Crystal Growth Data," Acta Cryst. D50:408-413 (1994).

Gonzalez, F. et al., "Crocodile: An Automated Apparatus for Organic Crystal Growth from Solution," Acta Astronautica 25(12):775-784 (1991).

Heinemann et al., "Scientific concepts: The Berlin Protein Structure Factory initiative," printed from http://www.rzpd.de/psf/s_concept2.html on Dec. 21, 2001 (16 pages).

Jancarik, J. et al., "Sparse matrix sampling: a screening method for crystallization of proteins," *J. Appl. Cryst.* 24:409-411 (1991).

Jing, H. et al., "New structural motifs on the chymotrypsin fold and their potential roles in complement factor B," *EMBO J.* 19(2):164-173 (2000).

Jing, H. et al., "Structures of Native and Complexed Complement Factor D: Implications of the Atypical His57 Conformation and Self-inhibitory Loop in the Regulation of Specific Serine Protease Activity," *J. Mol. Biol.* 282:1061-1081 (1998).

Jing, H. et al., "Structural basis of profactor D activation: from a highly flexible zymogen to a novel self-inhibited serine protease, complement factor D," *Euro. Mol. Bio. Org.* 18(4):804-814 (1999).

Jones et al., "Fully Automated Preparation of Hanging Drop Protein Crystallization Plates," abstract from ACA01 meeting printed from http://www.hwi.buffalo.edu/ ACA/ACA01/abstracts/text/W0352.html on Aug. 26, 2002 (1 page).

Jones, N., et al., "Apocalypse now: update on automated protein Crystallization using the new ACA vapor diffusion plate," *Acta CrystallogrA* (1987) 43 (Supplement): C275.

Kam et al., "On the Crystallization of Proteins," *J. Mol. Biol.* 123:539-555 (1978).

Kelders, H.A. et al., "Automated protein crystallization and a new crystal form of a subtilisin: eglin complex," *Protein Engin.* 1(4):301-303 (1987).

Koltay, P., "A Novel Fixed Volume Dispenser for the Massive Parallel Liquid Handling of Nanoliter Volumes," (Abstract for presentation scheduled for Oct. 25, 2001) printed from http://www.eurolabautomation.org on Apr. 11, 2002 (2 pages).

Korkhin, Y.M. et al., "Microseeding—Crystallization of a protein by microseeding after establishing its phase diagram," in Research Report 1 (Aug. 1995), printed from http://www.douglas.co.uk/rep1.html on Apr. 11, 2002 (6 pages).

Leonidas, D.D. et al., "Refined Crystal Structures of Native Human Angiogenin and Two Active Site Variants: Implications for the Unique Functional Properties of an Enzyme Involved in Neovascularisation During Tumour Growth," *J. Mol. Biol.* 285:1209-1233 (1999).

Llyod, L.F. et al., "Many Crystal Forms of Human Immunodeficiency Virus Reverse Transcriptase," *J. Mol. Biol.* 217(1):19-22 (1991).

Lowe, J. et al., "Capital Equipment MRC Laboratory of Molecular Biology Nov. 4, 2001" (4 pages).

Luft et al., "High Throughput Protein Crystallization: Keeping up with the Genomics,"(Abstract for presentation to be given at Gordon Research Conference "Diffraction Methods in Molecular Biology" on Jul. 3, 2000 at Andover, NH, USA)) printed from http://www.imca.aps.anl.gov/~ahoward/luft_ab.html (1 page).

Luft et al., "Macromolecular crystallization in a high throughput laboratory—the search phase," *J. Cryst. Growth* 232:591-595 (2001).

Luft et al., "Microbatch macromolecular crystallization in micropipettes," *J. Cryst. Growth* 196:450-455 (1999).

Luft et al., "Microbatch macromolecular crystallization on a thermal gradient," *J. Cryst. Growth* 196:477-449 (1999).

Luo, M., "Structural Genomics of C. elegans," (Abstract W0027 from ACA2002 Meeting) printed from http://www.hwi.buffalo.edu/ACA/ACA02/abstracts/text/W0027.html on Apr. 10, 2002 (1 page).

McPherson, A., "Crystallization of Macromolecules: General Principles," in *Methods in Enzymology* 114:112-120 (1985).

McPherson, A., "Crystallization of Proteins by Variation of pH or Temperature," in *Methods in Enzymology* 114:125-127 (1985).

McPherson, A., "Two approaches to the rapid screening of crystallization conditions," *J. Cryst. Growth* 122:161-167 (1992).

McPherson, A., "Use of Polyethylene Glycol in the Crystallization of Macromolecules," in *Methods in Enzymology* 114:120-125 (1985).

"High-Throughput Structure Determination in an Informatics Environment," (2001) printed from http://www.accelrys.com/webzine on Aug. 1, 2002 (4 pages).

Montelione, G.T. et al., "Structural genomics: keystone for a Human Proteome Project," *Nat. Struct. Biol.* 6(1):11-12 (Jan. 1999).

Morris, D.W. et al., "Automation of Protein Crystallization Trials: Use of a Robot to Deliver Reagents to a Novel Multi-Chamber Vapor Diffusion Plate," *Biotechniques* 7(5):522-527 (1989).

Mueller et al., "Development of a technology for automation and miniaturization of protein crystallization," *J. Biotech.* 85(1)7-14 (2001).

Newman, A.R., "Send in the Robots," *Anal. Chem.* 62(1):29A-34A (1990).

Nyarsik et al., "High Throughput Screening Station for Automated Protein Crystallization," (Abstract) (1 page).

Oldfield, T.J. et al., "A Flexible Approach to Automated Protein Crystallization," *J. Appl. Cryst.* 24:255-260 (1991).

Pebay-Peyroula, E. et al., "X-ray Structure of Bacteriorhodopsin at 2.5 Angstroms from Microcrystals Grown in Lipidic Cubic Phases," *Science* 277:1676-1681 (1997).

Perrakis, A. et al., "Protein microcrystals and the design of a micro-diffractometer: current experience and plans at EMBL and ESRF/ID13," *Acta Cryst.* D55:1765-1770 (1999).

Pusey, M. et al., "Growth Kinetics of Tetragonal Lysozyme Crystals," *J. Cryst. Growth* 76:593-599 (1986).

Pusey, M.L. et al., "Protein Crystal Growth—Growth Kinetics for Tetragonal Lysozyme Crystals," *J. Biol. Chem.* 261:6524-6529 (1985).

Rawas, A. et al., "Preliminary Crystallographic Studies on Duck Ovotransferrin," *J. Mol. Biol.* 208:213-214 (1989).

Rippon, G.D. et al., "Improved Microdroplet Method for Quantitative X-ray Microanalysis of Small Fluid Samples," *Micron* 24(1):17-21 (1993).

Rost, B., "Marrying structure and genomics," *Structure* 6:259-263 (1998).

Rubin, B. et al., "Minimal intervention robotic protein crystallization," *J. Cryst. Growth*. 110:156-163 (1991).

Sali, A., "100,000 protein structures for the biologist," Avalon Meeting Review, document generated Jan. 22, 1998, printed Apr. 1, 1999 from http://guitar.rockefeller.edu./avalon/review/avalon.html (7 pages).

Sanchez et al., "Protein structure modeling for structural genomics," *Nat. Struc. Biol.* (*Structural Genomics Supplement*) 986-990 (2000).

Santarsiero, B.D. et al., "Protein Micro-Crystallization Robotics System," W0251:Protein Micro-Crystallization Robotics System (09.07:Crystallization Techniques-Lectures-Room 106- Thursday, May 27 (Abstract for ACA99 meeting) printed from http://www.hwi.buffalo.edu/ACA/ACA99/abstracts/text/W0251.html on Feb. 28, 2002 (2 pages) (webpage indicates last updated on May 18, 1999).

Saridakis, E. et al., "Improving protein crystal quality by decoupling nucleation and growth in vapor diffusion," *Protein Sci.* 9:755-757 (2000).

Schuetz et al., "A novel nano-pipetting system for the development of high quality BioChip *arrays*," printed from www.tecan.com/la2000_nanopip.pdf (1 page).

Shapiro, L. et al., "The Argonne Structural Genomics Workshop: Lamaze class for the birth of a new science," *Structure* 6(3):265-267 (1998).

Shumate, "Low-volume (nanoliter) automated pipetting," *Am. Biotechnol Lab.* 11(6):14 (1993).

Sibille, L., et al., "Solvent evaporation rates in the closed capillary vapor diffusion method of protein crystal growth," *J. Cryst. Growth* 110:80-88 (1991).

Snell, E.H. et al., "Partial Improvement of Crystal Quality for Microgravity-Grown Apocrustacyanin $C_1$," *Acta Cryst.* D53:231-239 (1997).

Stevens et al., "Global Efforts in Structural Genomics," *Science* 294:89-92 (2001).

Stevens, "High-throughput protein crystallization." [review]. *Curr. Opin. Struct. Biol.* 10(5):558-563 (2000).

Stevens, R.C. et al., Research Proposal for development and testing of a system of robotics workstations dedicated to protein crystallization., E.O. Lawrence Berkeley National Laboratory and The Scripps Research Institute, pp. 2, 29-31, 33-52, unknown date.

Stevenson, "The world of Separation Science- Lab Automation '01: A Market Preparing for transition?," pp. 4-5 (2001).

Stewart et al., "Practical experimental design techniques for automatic and manual protein crystallization," *J. Cryst. Growth* 196:665-673 (1999), printed from http://www.douglas.co.uk/rat_des.html on Mar. 2, 2002 (12 pages).

Stura, E.A. et al., "Reverse Screening," *Acta Cryst.* D50:448-455 (1994).

Swartzendruber, J.K., et al., "Apocalypse: an automated protein crystallization system. III. In the beginning: The genesis of software," 1988) p. 81, Abstract PF5, Annual Meeting of the American Crystallographic Association, Philadelphia, PA.

Tebbutt J.S. et al., "Monitoring of crystallisation phenomena by ultrasound," *Electron. Lett.* 35(1):90-92 (1999).

Tisone, T.C., "Dispensing systems for miniaturized diagnostics," *IVD Technology Magazine*, printed from http://devicelink.com/ivdt/archive/98 (IVDI archive, May 98).

Tisone, T.C. et al., "The Role of Non Contact Microfluidics in High Throughput Protein Crystallization," (Abstract W0282 from ACA2002 Meeting) printed from http://www.hwi.buffalo.edu/ACA/ACA02/abstracts/text/W0282.html on Apr. 10, 2002(1 page).

van der Woerd, M. et al., "About Small Streams and Shiny Rocks: Macromolecular Crystal Growth in Microfluidics," (Abstract W0210 from ACA2002 Meeting) printed from http://www.hwi.buffalo.edu/ACA/ACA02/abstracts/texst/W0210.html.

van der Woerd, M.J., "Lab-on-a-chip Based Protein Crystallization [P-66]," *smallTalk 2001 Association for Laboratory Automation Final Conference Program*, San Diego, CA, held Aug. 27-31, 2001 (Abstract) (2 pages).

Varadarajan, R. et al., "Crystallographic Structures of Ribonuclease S Variants with Nonpolar Substitution at Position 13: Packing and Cavities," *Biochem.* 31(49):12315-12326 (1992).

Villasenor et al., "Fast Drops: A Speedy Approach to Setting Up Protein Crystallization Trials," (Abstract W0309) from ACA01 meeting printed from http://www.hwi.buffalo.edu/ ACA/ACA01/abstracts/text/W0309.html on Dec. 21, 2001 (1 page).

Ward, K.B. et al., "Automatic Preparation of Protein Crystals Using Laboratory Robotics and Automated Visual Inspection," *J. Cryst. Growth* 90:325-339 (1988).

Ward, K.B. et al., "Automating crystallization experiments," in Crystallization of Nucleic Acids and Proteins: A Practical Approach eds. A. Ducruiz & R. Giege, Oxford Univ. Press, New York, pp. 291-310.

Weber, P.C., et al., "Experiments with automated protein crystal growth," (1987) p. 28, Abstract H5, Annual Meeting of the American Crystallographic Association, Philadelphia, PA.

Weber, P.C., "Overview of Protein Crystallization Methods," *Methods in Enzymology* 276:13-22 (1997).

Wilson, S.A. et al., "Crystallization of and Preliminary X-ray Data for the Negative Regulator (AmiC) of the Amidase Operon of *Pseudomonas aeruginosa*," *J. Mol. Biol.* 222(4):869-871 (1991).

Yakovlev, Y.O. et al, "A Laboratory Apparatus for Crystal Growth from Solution," *Instruments and Exp. Tech.* 41(2):292-296 (1998).

Yegian, D., "Task-specific robotics for sample loading, centering and retrieval," printed from http://smb.slac.stanford.edu/jcsg/robotics/abstracts/dy_abs.html on Apr. 12, 2002 (1 page) (site last modified Oct. 16, 2000).

Zeelen, J. Ph. et al., "Crystallization Experiments with 2-Enoyl-CoA Hydratase, Using an Automated 'Fast-Screening' Crystallization Protocol," *Acta Cryst.* D50:443-447 (1994).

Zeppezauer, M., "Microdiffusion cells for the growth of single protein crystals by means of equilibrium dialysis," *Arch. Biochem. Biophys.* (1968) 564-573.

Advertisement: "The first Fully Automated Digital Imaging System specifically for crystallographers—CrystalScore. Cyber Lab," ACA Newsletter 1:28 (Spring, 2000).

"BMST Pervasive Technologies—Concept Paper, BMST Initiative Thrust Area: Emerging of Breakthrough Process Technologies—Definition of the Thrust Area—NACFAM," printed from http://www.nacfam.org/bmst/bmstemergingtechnolgies.html on Feb. 26, 2002 (5 pages).

Brochure: Automatic Protein Crystallization System. Douglas Instruments Limited. (1990)(4 pages).

Catalog, 63 pp., Hampton Research Corporation (copyright 1999).

"Hampton Research—Solutions for Crystal Growth," printed from http://www.hamptonresearch.com on Feb. 22, 2001 (2 pages).

"High throughput protein crystallization—EMBL Practical Course on Protein Expression, Purification and Crystallization—Aug. 14-20, 2000 EMBL Outstation Hamburg, Germany," printed from http://www.structure.llnl.gov/Xray/tutorial/High_Throughput_EMBL_full.html on Apr. 12, 2002 (10 pages).

"Meeting Summaries," printed from http://www-nmr.cabm.rutgers.edu/labdocuments/mtgsummaries/mtgsummaries.html on Apr. 12, 2002 (32 pages).

Meeting Summary: "NIGMS Structural Genomics Project Planning Meeting—The Protein Structure Iniative, Bethedsa, MD, Nov. 24, 1998," printed from http://www-nmr.cabm.rutgers.edu/labdocuments/mtgsummaries/nigms/nigms.html on Apr. 12, 2002 (17 pages).

Meeting Summary: "NIH Protein Structure Initiative Meeting: Target Selection, Feb. 1999, Washington, D.C." printed from http://www-nmr.cabm.ruters.edu/labdocuments/mtgsummaries/nih_prot_struct_init/nih on Apr. 12, 2002 (23 pages).

"Minutes May 1-2, 2001—Biological and Environmental Research Advisory Committee (BERAC)," printed from http://www.er.doe.gov/production/ober/berac/5-01mins.html on Apr. 12, 2002 (10 pages).

News Release: "Large-scale Xn: 'The use of Microbatch for Large Scale Crystallization Projects,'" Douglas Instruments, Hungerford, UK (indicated on website as news from Feb. 1999), printed from http://www.douglas.co.uk/proposal.html on Feb. 22, 2001 (5 pages).

"NIGMS—Advisory Council Meeting Minutes, 5-98—Minutes of the National Advisory General Medical Sciences Council—May 14-15, 1998," printed from http://www.nigms.nih.gov/about_nigms/council_may98.html on Apr. 12, 2002 (10 pages) (site last updated Jul. 17, 1998).

"NIGMS—NIGMS Structural Genomics Targets Workshop Feb. 11-12, 1999" printed from http://www.nigms.nih.gov/news/meetings/structural_genomics_targets.html on Apr. 12, 2002 (18 pages).

"NIGMS Protein Structure Initative Meeting Summary Apr. 24, 1998," printed from http://www.nigms.nih.gov/news/reports/protein_structure.html on Apr. 12, 2002 (12 pages) (site last updated Jun. 2, 1998).

Presentation by Chair Graham Fleming, University of California, Berkeley: "Working Group on Biosciences," pp. 175-198, printed from http://www-als.lbl.gov/als/workshops/scidirecthtml/9BioSci.Word_Work_File_L_646, index of /als/workshops/scidirecthtml/9BioSci indicates file available in multiple formats, indicates file last modified Nov. 1998.

Presentation: NASA, Marshall Space Flight Center—Lab-on-a-Chip Based Protein Crystallization, by van der Woerd, M., dated Oct. 25, 2001, printed from worldwideweb in 2002 (27 pages).

Press Release: "RAMC 1999—Presentation Abstracts. Presentations T1-T16." printed from http://www.hamptonresearch.com/stuff/RAMC99/RAMC99TA.html on Apr. 8, 2002 (11 pages).

Press Release: "RAMC 2001—Poster Abstracts," printed from http://www.hamptonresearch.com/stuff/RAMC01/RAMC01PA.html on Apr. 10, 2002 (17 pages).

Press Release: LabAutomation 2001—Annual Conference and Exhibition—LabAutomation2002—Jan. 26-30, 2002—Palm Springs California—"Preliminary Poster Program" printed on Apr. 11, 2002 from http://labautomation.org.LA/LA02/program/action.lasso?-database=LA2002Abs&-layout Apr. 11, 2002d (166 pages).

Press Release: "RAMC 2001—Presentation Abstracts. Presentations T1-T15" printed from http://www.hamptonresearch.com/stuff/RAMC01/RAMC01TA.html on Apr. 8, 2002 (12 pages).

Press Release: "Research and Innovation: Genomics Institute of the Novartis Research Foundation (GNF), Novartis Institute for Genomics," (copyright, 1999) printed from http://www.pharma.novartis.com/research on Dec. 18, 2001 (2 pages).

Oct. 2, 2002Press Release: "Minutes Apr. 22-23, 1999—Biological and Environmental Research Advisory Committee (BERAC)," this meeting was announced in the Federal Register for Apr. 22-23, 1999 (Public Law 92-463, 86 Stat. 770) American Geophysical Union, Washington, D.C., printed from http://www.er.doe.gov/production/ober/berac/4-99mins.html on Apr. 12, 2002 (8 pages).

Press Release: "Structural Biology—Charge Jun. 10, 1997—Report of the Structural Biology Subcommittee of the Biological and Environmental Research Advisory Committee—In response to the charge letter of Dr. Martha Krebs, Jun. 10, 1997," printed from http://www.er.doe.gov/ production/ober/berac/final697.html on Feb. 26, 2002 (29 pages).

Press Release: Structural Biology, Charge May 28, 1998—Report of the Structural Biology Subcommittee of the Biological and Environmental Research Advisory Committee—In response to the charge letter of Dr. Martha Krebs, May 28, 1998 Executive Summary—Improvements recommended for current beamlines http://www.er.doe.gov/production/ober/berac/final598.html (11 pages).

Press Release: "TECAN Compound dissolution—Automating Drug Discovery at Zeneca," (Oct. 1998) printed from http://www.tecan.com/pr/tec_pr_DDElisa.html on Apr. 15, 2002 (1 page).

Press Release: "Crystallomics Core @ JCSG—Crystallomics Core," printed from http:// bioinfo-core.jcsg.org/bic/links/crystallomics.htm on Feb. 25, 2002 (2 pages with page indicating links last updated Apr. 18, 2001).

Press Release: Tecan Genesis NPS—Nanopipetting for plate and array-based applications: *Miniaturize your Application with GENESIS NPS* printed from. http://www.tecan.com/tec_main_nps.html on Apr. 13, 2002 (3 pages).

Press Release: "Tecan Genesis Workstation—Genesis Workstation," printed from http://www.tecan.com/tec_main_genesis_workstation.html on Apr. 15, 2002 (1 page).

Press Release: Functional Genomics. http:// www.bmb.psu.edu/simpson/16genome/Function.html (1 page).

Press Release: "For Immediate Release (Sep. 25, 2000): Joint Center for Structural Genomics Funded to Advance High-Throughput Protein Structure Determination," printed from http://www.sdsc.edu/Press/00/092600.html on Feb. 20, 2002 (3 pages).

Press Release: "Berkeley Lab Research Review Summary 2000—The Crystal Robot," by Preuss, P., printed from http://www.lbl.gov/ Science-Articles/Research-Review/Magazine/2000/Winter/features on Feb. 28, 2002 (3 pages).

Press Release: "Winners—NASA Selects Research Proposals in Cellular and Macromolecular Biotechnology" printed from http://research.hq.nasa.gov/code_u/nra/current/NRA-00-HEDS-03/winners.html on Apr. 8, 2002 (5 pages).

Press Release: Minutes Nov. 5-6, 1998—Biological and Enivornmental Research Advisory Committee (BERAC). The meeting was announced in the Federal Register for Nov. 5-6, 1998 (Pub. L. No. 92-463, 86 Stat. 770) American Geophysical Union, Washington, D.C., printed from http://www.er.doe.gov/production/ober/berac/11-5-98mins.html on Apr. 12, 2002 (15 pages).

Press Release: East of England Innovation Relay Centre: Pharma—Technology Offers from Europe, particularly High-throughput protein crystallization screening and polymorph screening (Reference: PAN4159) on p. 15 of document printed from http://www.stjohns.co.uk/eeirc/pharma%20offers.htm on Apr. 11, 2002 (32 pages).

Press Release: Stewart, P.S. et al., "Using Microbatch for Large-Scale Crystallization Projects," Large-scale xn—visual—printed from http://www.douglas.co.uk/glasgow.htm Aug. 1, 2002 (3 pages).

Press Release: Tecan Product News—Product News from 1998, printed from http://www.tecan.com/tec_main_product_news_98.html on Apr. 13, 2002 (3 pages).

Press Release: Tecan Product News—Product News from 1999, printed from http://www.tecan.com/tec_main_product_news_99.html on Apr. 13, 2002 (3 pages).

Press Release: Tecan Product News—Product News from 2000, printed from http://www.tecan.com/tec_main_product_news_00.html on Apr. 13, 2002 (2 pages).

Press Release: "Products—Products Feb. 2001," printed from http://www.douglas.co.uk/products.html on Mar. 2, 2002 (2 pages).

Press Release: High-throughput protein crystallization screening and polymorph screening. http://www.steinbeis-europa.de/db/ircnet_details.php?BEREICH=LIFE&TYP=Offer&BB (Abstract).

Press Release: "PBD/Research/Research Areas/AUTOMATION," printed from http://www.lbl.gov/ LBL-Programs/pbd/xl_research/automation.html on Feb. 28, 2002 (4 pages).

Press Release: "The Robot—X-ray Crystallography in Leiden," printed fro http://www.chem. Leidemuniv.nl/bfsc/robot.html on Mar. 2, 2002 (2 pages).

Press Release: "The Scripps Research Institute—News and Views—Life After the Human Genome Project: TSRI Researchers Spearhead Protein Structure Initiative," by Mike Ono Benedyk, printed from http://www.scripps.edu/newsandviews/e_20010226/print-jcsg.html on Feb. 28, 2002 (3 pages).

Press Release: "Bringing the Genome to Life Report—From the Archives: Bringing the Genome to Life—Energy Related Biology in the New Genomic World. A New Research Program for the Department of Energy's Office of Biological and Environmental Research recommended by the Biological and Environmental Research Advisory Committee. (Jun. 2000)" printed from http://doegenomestolife.org/history/genome-to-life-rpt.html on Apr. 12, 2002 (23 pages).

Press Release: Letter to DOE Health and Environmental Research Advisory Committee Chairman dated Jun. 10, 1997, printed from http://www.er.doe.gov/production/ober/berac/97stbio.html on Feb. 26, 2002 (2 pages).

Press Release: "Response to a Dec. 8, 2000, charge from the Director of the DOE Office of Science," printed from http://www.er.doe.gov/production (19 pages).

Press Release: Letter to DOE Health and Environmental Research Advisory Committee Chairman dated May 28, 1998, printed from http://www.er.doe.gov/production/ober/berac/stbiochg.html on Feb. 26, 2002 (2 pages).

Press Release: "System Users—IMPAX and Oryx Users Feb. 2002," printed from http://www.douglas.co.uk/users.htm on Mar. 2, 2002 (3 pages).

Press Release: "Large-scale Xn—The use of Microbatch for Large-Scale Crystallization Projects," by Douglas Instruments printed from http://douglas.co.uk./proposal.htm on Apr. 11, 2002 (5 pages).

Report entitled, "Physical Biosciences Division," particularly section entitled "Protein Microcrystallization Robotic System," (pp. 14-17), printed from http://www-nsd.lbl.gov/LBL-Publications/LDRD/1998/PB/index.html#Jaklevic, on Aug. 28, 2002, page indicated as last modified on Feb. 19, 1999 (17 pages).

Section of Report entitled, "Protein Microcrystallization and Structure Determination," printed from http://www-nsd.lbl.gov/LBL-Publications/LDRD/1999/PBD.html#Stevens on Aug. 28, 2002, page indicated as last modified on Apr. 4, 2000 (3 pages).

Webpage: "Harvesting, Harvesting Crystals from Microbatch for Cryocrystallography," Douglas Instruments—Research Report 3, Oct. 1995, printed from http://www.douglas.co.uk/rep3.htm on Apr. 11, 2002 (4 pages).

Website: "Publications—Journals—Trade Journals: Events Index—Abstracts and Proceedings—Achema 2000," printed from http://www.combichem.net/files/abstract1.htm on Aug. 1, 2002 (18 pages).

Webpage: Eickhoff et al., "An Automated Platform for Miniaturized protein Crystallization," Greiner Bio-One (Abstract), date of last modification on web indicated as Mar. 30, 2001, printed May 2002 (1 page).

Website: "A day on High-Throughput Techniques in Structural Biology," printed from http://www.embl-heidelberg.de/courses/StructureSolution02/satellite.html (5 pages) text dated Aug. 1998 and Feb. 1999.

Website: "A Recipe to grow crystals of lysozyme by the gel acupuncture technique: Granada Crystallization Box," printed from http://lec.ugr.es/GranadaCrsytBox/GCB on Apr. 11, 2002 (7 pages).

Website: *Bio*Robotics http://www.biorobotics.com (Pamphlet), printed on Oct. 7, 1999 (12 pages).

Website: "Differences—The Major Differences between Oryx 6 and IMPAX 1-5," Douglas Instruments, dated Mar. 2001), printed from http://www.douglas.co.uk/differn1.htm on Apr. 11, 2002 (1 page).

Website: "General Interest II—Invited Abstracts," (Jul. 26, 2001) printed from http://www.hwi.buffalo.edu/ACA/ACA01/abstracts on Apr. 13, 2002 (2 pages).

Website: "Harima Workshop on Implementation for High-throughput Structure Determination by Protein Crystallography—Present Status and Future Goal—A Satellite of International Conference on Structural Genomics 2000 at Spring-8." printed from http://www.spring8.or.jp/english/conference on Dec. 19, 2001 (4 pages).

Website: "Impax: IMPAX 1-5 for Crystallization with Microbatch". printed from http://www.douglas.co.uk/impax.htm on Mar. 2, 2002.

Website: "News" printed from http://www.douglas.co.uk/news.htm on Apr. 15, 2002 (2 pages).

Website: "Oryx 6—Using Oryx 6 for Crystallization with Microbatch: Microbatch operation in identical to IMPAX 1-5" printed from http://www.douglas.co.uk/oryx.htm.

Website: "PhysicsWeb—Protein crystallography: the human genome in 3-D," http://physicsweb.org/article/world/11/5/8 (May 1998), printed from website Apr. 11, 2002 (9 pages).

Webpage: "Poster Session 7—Genomics, Proteomics and New Target Discovery," The Society for Biomolecular Screening—7th Annual Conference and Exhibition (2001), see #7014-7015, printed from http://www.hwi.buffalo.edu/ (5 pages).

Website: Garcia-Ruiz, J.M., "The role of gravity in protein crystallization: Is there an effect of gravity on the crystallization process," printed from http://lec.ugr.es/esatt/Role_of_gravity/Role.htm on Apr. 11, 2002 (3 pages).

Website listing products available from Gilson, printed http://www.gilson.com/cyberprd.htm on Feb. 22, 2001 (1 page).

Website listing Abstracts for Oral Presentations: S7—Instrumentation—Instrumentation and Techniques for crystallization. pp. 1-3 (Nancy 2000 XIX European Crystallographic Meeting (held Aug. 25-31).

* cited by examiner

METHOD FOR SCREENING CRYSTALLIZATION CONDITIONS IN SOLUTION CRYSTAL GROWTH

This application is a continuation of, and claims the benefit of, application Ser. No. 09/543,326, filed Apr. 5, 2000, abandoned, which is hereby incorporated herein in its entirety by references, and claims priority from U.S. application Ser. No. 60/128,018, filed Apr. 6, 1999.

FIELD OF THE INVENTION

The present invention relates to the crystallization of proteins in or from protein solutions. The present invention particularly relates to a method of screening a large number of protein crystal growth conditions which may be conducive to protein crystallization. Even more particularly, the present invention relates to a method which identifies one or more optimum protein crystal growth conditions, while at the same time using substantially less protein solution.

BACKGROUND OF THE INVENTION

The crystallization of proteins for structure-function studies and structure based drug design has become an increasingly important part of biotechnology research. When crystal growth is attempted for a new protein, the appropriate chemical conditions (i.e. protein concentration in solution, precipitate type and concentration, pH, and growth temperature) are unknown and have typically been determined by trial and error experimentation.

Typically 1000 or more different sets of crystal growth conditions are screened to determine conditions conducive to crystallization. The screening involves repetitive procedures that are extremely laborious and tedious. With present laboratory protein crystal growth equipment, each crystallization chamber requires about one micro-liter of protein solution. The protein solutions typically have concentrations in the range of 10 to 25 micrograms per microliter to facilitate crystal growth. Therefore, to screen 1000 samples typically requires between 10 and 25 milligrams of protein. This is a considerable and costly amount, especially for proteins that are difficult to isolate or generally express. A large percentage (about 50%) of the proteins cannot easily be expressed in milligram quantities.

Thus, it would be desirable to provide methods for screening protein crystal growth conditions that require picogram to microgram amounts of protein for each screening condition. Preferably such methods would require only picogram to nanogram amounts of protein in picoliter to nanoliter volumes in each screening condition sample.

It would be further desirable to provide high throughput screening methods for screening protein crystal growth conditions in a large number of samples on a sub-microgram scale. These methods would use a microarray as a platform for protein crystal growth. The methods would also utilize automatic dispensing of solutions and scoring of crystal growth.

SUMMARY OF THE INVENTION

The present invention is a method of screening protein crystal growth conditions employing a minimal amount of protein, preferably on a picogram to microgram scale. Each screening sample has picogram to microgram amounts of protein in a picoliter to nanoliter volume. Predetermined protein crystal growth conditions are maintained and crystal growth is analyzed using both qualitative and quantitative criteria.

In a preferred embodiment, a microarray is provided for use in methods of screening protein crystal growth. Preferably the microarray has a plurality of micro-chambers in the microarray. The micro-chambers may be passive or a combination of passive micro-chambers that are connected with miniaturized active control elements such as, but not limited to, valves, pumps and electrodes. A protein solution is automatically dispensed into the micro-chambers. The protein crystal growth conditions of each of the micro-chambers is adjusted so that the protein crystal growth conditions of at least two of the micro-chambers differs. Protein crystal growth in the micro-chambers is then analyzed based on both the qualitative amount of crystallization and the quality of the crystals formed.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF INVENTION

Figure 1:
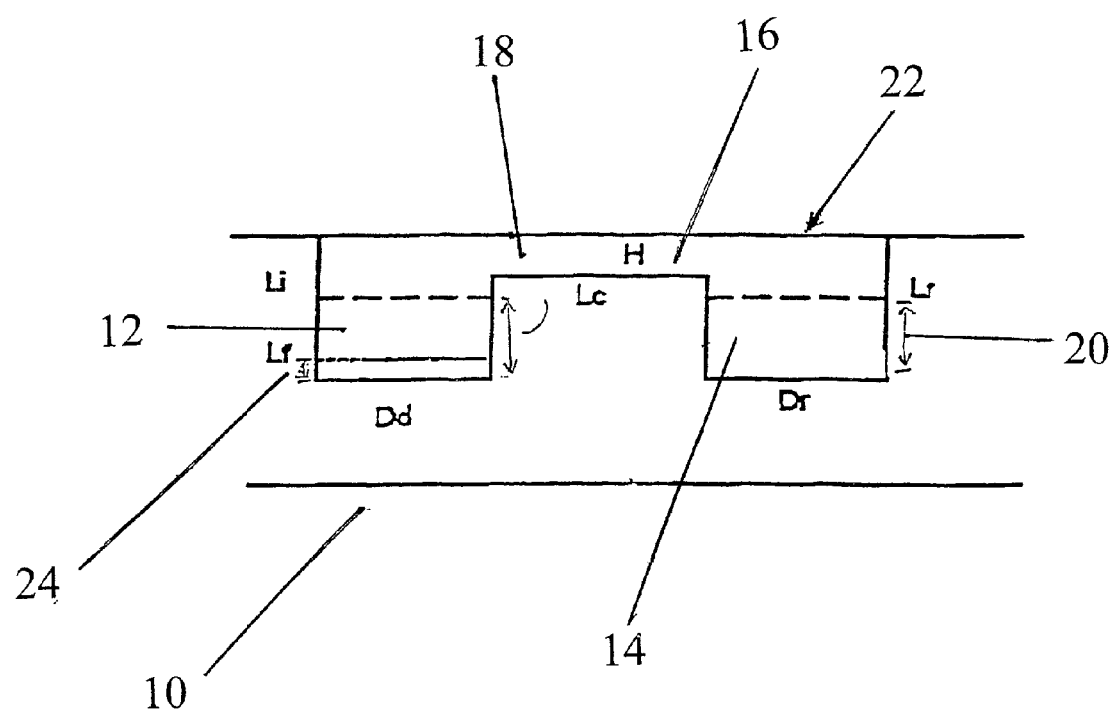
FIG. 1 is a schematic illustrating a two well design in a microarray.

The method of the present invention is for screening protein crystal growth conditions in protein solutions employing a minimal amount of protein in a minimal volume, preferably on a pico, nano or meso scale. Pico, nano or meso scale as used herein preferably employs (on average) picogram (pg), nanogram (ng) or microgram (μg) amounts of protein in picoliter (pl) or nanoliter (nl) volumes. Preferably, the amount of protein in each screening sample is less than about 5 μg. More preferably, the amount of protein in a screening sample will be less than about 1 μg. In one embodiment, the volume of protein solution in a screening sample is preferably from about 0.001 nl to about 250 nl and more preferably about 0.01 nl to about 10 nl. It will be appreciated by those skilled in the art that the volumes actually employed for any particular protein will be a function of (without limitation) the target protein and its concentration in the protein solution.

The protein solution contains one or more desired proteins for crystallization. As used herein, the term "protein" is meant to include all naturally occurring and synthetic peptides, polypeptides, proteins, and protein complexes. In one preferred embodiment the concentration of protein in the solution is from about 0.1 µg/µl to about 50 µg/µl, more preferably from about 0.1 µg/µl to about 10 µg/µl, and still more preferably about 0.1 µg/µl to about 1.0 µg/µl. In another preferred embodiment, the solution is buffered to a pH between about 2.0 and about 10.0, more preferably from about 3.0 to about 8.5. If desired, the protein solution may optionally contain agents that aid in solubilizing the protein at the desired protein concentration or conditions. For example, if the protein is a membrane protein, the protein solution may optionally contain one or more surface active agents, such as a detergent mixture. In one preferred embodiment, the protein solution also comprises components that assist in crystallization. By way of non-limiting example, the protein solution will comprise an aqueous salt solution, polyethylene glycol, or an alcohol. Such components as well as their selection, ranges, contraindications and the like are well known to those skilled in the art. See, for example, Gilliland, G. L. et al., *Acta Crystallogr.* D50:408-413 (1994); McPherson, A., *Crystallization of Biological Molecules,* Cold Spring Harbor Press, Cold Spring Harbor, N.Y., pp. 487-524 (1999), expressly incorporated by reference.

The protein solution is dispensed onto a platform. The platform can be, by way of non-limiting example, a glass slide, a multi-well plate or a microarray. The solution is preferably dispensed using a device with picoliter or nanoliter accuracy. Preferably the dispensing device has at least a 90% accuracy on a picoliter or nanoliter scale. The protein solution can be dispensed manually using, for example, a syringe. In a highly preferred embodiment, automatic dispensing devices are used to dispense the protein solution.

A second solution, the reservoir or precipitate solution is provided. The precipitate solution is a solution that helps to bring about protein crystallization. It can comprise, for example, a salt solution, an alcohol or a polyethylene glycol. The second solution is provided either before, after, or simultaneously with the protein solution. The volume of the precipitate solution is typically equal to or greater than the volume of protein solution. The placement of the second solution is dependent on the crystallization method used but is typically in fluid communication with the first solution. Fluid communication can be liquid-liquid, liquid-vapor or vapor-vapor communication. Generally, a channel is provided for fluid communication. A channel is broadly defined herein as a space that enables fluid communication to occur. In the liquid-liquid diffusion method, the protein solution and precipitate solution contact each other at an interface. In batch crystallization, the two solutions are mixed together. If vapor diffusion crystallization is desired, the two solutions are kept separate but space is allowed for the diffusion of vapor between the solutions. Or, in an alternate embodiment, a single source or reservoir of the second solution may be employed. In yet another alternate embodiment, a desiccant source or a dry gaseous reservoir may be employed in place of the second solution. Specific conditions and variations in these methods are well known to the skilled artisan.

Protein crystal growth is monitored periodically, either qualitatively, quantitatively, or both. This may be by manual inspection using high resolution microscopy or electron microscopy. Preferably, protein crystal growth may be monitored automatically, by, for example, high resolution optical means which automatically detects crystal growth based on, for example, edge analysis. If desirable crystal growth is observed in a sample, the protein crystal growth conditions of that sample can be reproduced on a macro scale to produce a protein crystal for further analysis. Alternatively, if a precipitate or a clear sample is observed, these conditions can be used to optimize the conditions for additional screening. It will be appreciated that the platform must employ at least one path that is visually and/or optically clear to the method of detection.

In at least one preferred embodiment the method of the present invention for screening protein crystal growth employs a microarray with a plurality of wells or reservoirs as the platform. A microarray may be constructed, for example, similar to a micro-electromechanical chip. The microarray preferably has a planar shape and employs a size and thickness that are compatible with manual or automated plate grippers. The microarray can be made from different materials and by different techniques known to those skilled in the art. The material of the microarray that includes the wells or reservoirs is preferably minimally water absorbing, and is otherwise sufficiently unreactive with the components of the solution. This may be done as a laminate or provided as a coating, for example. Alternatively, a material that absorbs water at a predictable rate can also be used to construct the wells or reservoirs. The volumes of protein and precipitate solutions may then be adjusted to compensate for the water absorption of the material. Preferred materials include, but are not limited to, glass, fused silicon, quartz, a silicon wafer, a polymer or a polysulphone. Alternatively, the microarray can be made from a material coated with a hydrophobic material, such as polysulphone, to limit water absorption in the microarray. Alternatively, the microarray comprises more than one material. Preferably, the microarray is a composite with a bottom of thin glass plate bonded to plastic, glass, silicon rubber or other materials in which wells can be manufactured, with at least one side providing an optical path that is acceptable to the detection technique employed.

In an alternate embodiment, the surfaces of the wells are hydrophobic. For example, the material of the microarray may have a hydrophobic surface. Alternatively, the surfaces of the wells may be coated with a hydrophobic coating. Although not necessary, the hydrophobic surfaces of the wells prevent the drops of solutions from spreading.

The microarray includes a multitude of micron sized wells on the surface of the chip. The term wells encompasses wells, micro-chambers and any indentation sufficient of holding or retaining a desired volume of from about 0.001 nl to about 500 nl, preferably from about 0.01 nl to about 20 nl. The wells are spaced from each other on the surface. The precise number of wells on the surface of the microarray can vary, and the total number of wells on the surface is a matter of choice for the user.

Each of the wells has a volume sufficient to hold an amount of protein solution adequate for growing a protein crystal. Preferably, each of the wells holds a volume from about 0.001 nl to about 250 nl, preferably from about 0.01 nl to about 10 nl.

The wells of the microarray are made by using an etchant such as hydrogen fluoride or by other known etching or fabrication-techniques.

The wells can include known means for controlling conditions, individually or collectively, such as pressure, heating or cooling the wells, humidity levels in the wells as well as known means for stirring materials loaded into the wells.

Figures 2A, 2B, 2C:
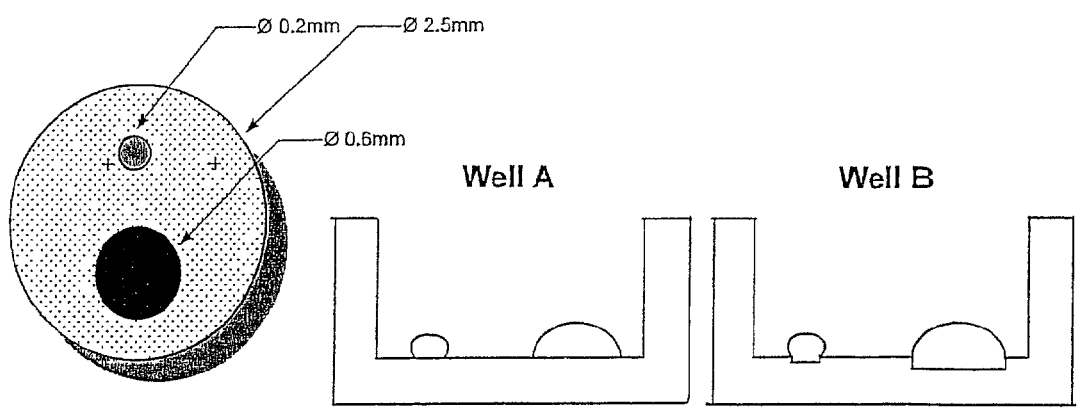
FIG. 2A is a schematic showing a top view of the placement of protein and precipitate solutions in a one well design.
FIG. 2B is a schematic showing a side view of placement of protein and precipitate solutions in a one well design.
FIG. 2C is a schematic showing a side view of an alternative placement of protein and precipitate solutions in one well.
Figures 2D, 2E:
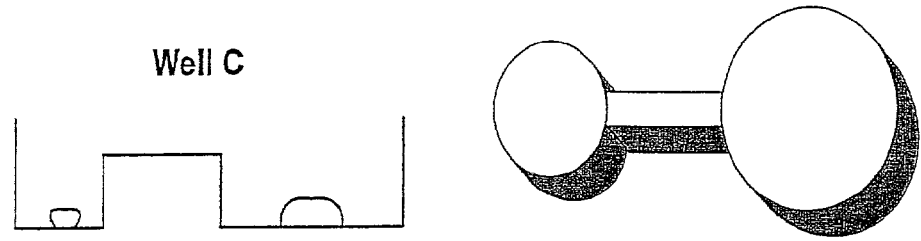
FIG. 2D is a schematic showing a side view of placement of protein and precipitate solutions in two wells.
FIG. 2E is a schematic showing a top view of the placement of protein and precipitate solutions in a two well design.

In one arrangement, the wells of the microarray are not connected and separate from each other. In an alternative arrangement, adjacent wells of the microarray are connected by one or more channels which provide fluid communication between the adjacent wells (FIGS. 1 and 2D-E). Preferably, the connecting channels will have cross-section dimensions and length allowing control over the rate of transport of fluid, vapor, buffer, or precipitating or crystallizing agents through the channels. In one embodiment, varying the dimensions of the channels controls protein crystal growth condition. In an alternate embodiment, protein crystal growth conditions are controlled by placing a material in the micro-channels that controls fluid communication between the wells. Non-limiting examples are membranes, acrylamide or agarose. For example, the connecting micro-channels are from about 0.0001 to about 0.2 microns wide and from about 0.00005 to about 0.1 microns deep. Alternatively, the micro-channels are from about 0.0001 to about 2.0 microns wide and from about 0.00005 to about 0.5 microns deep. The micro-channels are formed in the microarray chip by the known etching techniques.

An example of two wells in a microarray (10) connected by a micro-channel is shown in FIG. 1. The protein solution well 12 is connected to precipitate solution well 14 by a microchannel 16. The dimensions of each well are designed to hold the desired amount of solution and may have the same or different dimensions. Initially, protein sample is dispensed into well 12 to an initial liquid height 18 and precipitate solution is dispensed into well 14 with liquid height 20. The top of the wells and microchannel are sealed by an optically clear cover 22. In vapor diffusion crystallization, the precipitate solution in well 14 has a lower vapor pressure than the protein solution in well 12, causing diffusion of solvent from well 12 to well 14 until the solution liquid height in well 12 reaches a final height 24. The concentration of the protein solution in well 12 precipitates protein crystal formation.

The microarray can also include a known means for transmitting a fluid or gas to the wells of the microarray from an external source. For example, an external mechanical pumping system marketed by Watson-Marlowe, Inc., under the trade designation "205U" can be used. The pumping system is a multi-channel cassette which delivers fluid or gas in reproducible and accurately controlled amounts. optionally, micro-valves are disposed in the wells and micro-channels to regulate the flow of fluid or vapor between the wells and through the micro-channels in a known manner.

An automated dispensing mechanism capable of accurately and/or repeatedly dispensing picoliter and/or nanoliter volumes is also provided. Preferably, the automated dispensing mechanism has an accuracy of at least about 90%. The automated dispensing mechanisms are preferably Piezo-based or fast solenoid dispensing mechanisms. More preferable, the dispensing mechanism is a fast solenoid dispensing mechanism. The dispenser has a large number of parallel capillaries. The capillaries are in fluid communication with a source of protein solution, a source of precipitate solution, and a source of buffer solution. The dispensing can be actuated by ultrasonic transducers that efficiently produce a pressure wave in the capillaries that contain the solutions. The dispenser is analogous to ink jet printer heads for computer printers but the fluid is not heated, thus not damaging the solutions.

The protein solution preferably comprises an aqueous protein solution at a concentration of from about 0.1 μg/μl to about 50 μg/μl. Preferably, the concentration is from about 0.1 μg/μl to about 10 μg/μl, more preferably from about 0.1 μg/μl to about 1.0 μg/μl. Preferably, the protein solution comprises a detergent mixture when crystallizing membrane proteins. The precipitate solution preferably comprises a concentrated aqueous salt solution or polyethylene glycol as precipitating agents. The buffer solution preferably has pH between about 2 and about 10.

The automated dispensing mechanism dispenses an initial volume of protein solution, an initial volume of precipitate solution, and an initial volume of buffer solution from the source of protein solution, the source of precipitate solution, and the source of buffer solution, respectively, into preselected wells or connecting channels of the microarray.

The placement of the initial volume of protein solution, the initial volume of precipitate solution, and the initial volume of buffer solution in the preselected wells or channels of the microarray is dependent upon the method utilized to effect crystallization of the protein in the protein solution.

Preferred methods to effect crystallization of the protein in the protein solution include liquid-liquid diffusion, batch diffusion, and vapor diffusion.

In the liquid-liquid diffusion method, the initial volume of protein solution is placed in one set of preselected wells, and the initial volume of precipitate solution is placed in a separate or different set of wells. The protein solution wells are connected to the precipitate solution wells by micro-channels. The initial volume of buffer solution may be placed in the micro-channels, or alternatively added directly to the initial volume of protein solution and/or precipitate solution.

The concentration, amounts, precipitate type, and pH of the initial volumes of protein solution, precipitate solution, and buffer solution are primary conditions which determine protein crystal growth in a protein solution. In preparing the initial solutions, and in the automated dispensing mechanism placement, these conditions and the sample placement are varied in accordance with a pre-designed program.

A cover plate is affixed to the microarray to convert the wells to micro-chambers and to convert the micro-channels to a capillary tube structure. The cover plate can made of the same or different material as the microarray, but the cover plate (or some portion of the well or chamber) must be transparent to permit optical analysis of the protein solutions in the chambers of the microarray. Preferably, the cover plate will be glass or other material that is visually or optically clear, such as an optically clear tape.

Alternatively, the environment surrounding the microarray can be controlled to limit evaporation of the solutions. Under controlled conditions of, for example, temperature and humidity, covering the samples may not be necessary.

The crystallizing agent in the precipitate solution, in selected micro-chambers, diffuses via the connecting capillaries to selected micro-chambers containing protein solution.

Protein crystal growth in the different chambers are then monitored by high resolution or other optical means which automatically detects crystal growth based on well known edge analysis. Alternatively, the protein crystal growth can be monitored by manual inspection using high resolution microscopy or electron microscopy. Preferably the protein crystal growth in the chambers is monitored by high resolution optical means which automatically detects crystal growth based on edge analysis.

Once crystal growth in a chamber is detected, that chamber's protein crystal growth conditions can be reproduced on a macro scale to produce a protein crystal which can be analyzed by x-ray crystallography. Alternatively, if a precipitate or clear sample is observed, the conditions in those samples can be used to optimize conditions for additional screening.

In the vapor diffusion method, the initial volume of protein solution is placed in one set of preselected wells, and the initial volume of precipitate solution is placed in a separate or different set of wells based on a pre-designed program, as with the liquid-liquid diffusion method (FIGS. 2D-E). The protein solution wells are connected to the precipitate solution wells by micro-channels. The initial volume of buffer solution is added to the initial volume of protein solution and/or initial volume of precipitate solution. Alternatively, the protein solution and precipitate solution can be placed in the same well such that the two solutions do not come into contact (FIGS. 2A-C).

As with liquid-liquid diffusion, the crystal growth is varied in different wells in accordance with a pre-designed program in which the placement, concentration, amounts, precipitate type, and pH conditions are varied in the different wells.

A cover plate is then affixed to the microarray as with the liquid-liquid diffusion method. The vapor pressure of the precipitate solution is lower than the vapor pressure of the protein solution. This causes the protein solution in a microchamber which is connected via a capillary to a microchamber containing a precipitate solution to evaporate and become super-saturated causing precipitation of protein. Crystal growth is monitored as in the liquid-liquid diffusion.

Alternatively, the protein solution is placed into wells of the microarray and the microarray is exposed to a single reservoir with the precipitate solution. This method allows for less fluid dispensing, but also less control of the protein crystal growth conditions with respect to each protein sample.

In the batch method, the volume of protein solution, the volume of precipitate solution, and the volume of buffer solution are placed together in individual wells of the microarray. In this method, the chip does not have connecting channels between the wells.

As with liquid-liquid diffusion and vapor diffusion methods, the crystal growth is varied in different wells in accordance with a pre-designed program in which the placement, concentration, amounts, precipitate type, and pH conditions are varied in the different wells.

As with liquid-liquid diffusion and vapor diffusion methods, a cover plate is affixed to the microarray, and the crystal growth is then monitored.

If desired, fluid or gas can delivered to the micro-chambers in reproducible and accurately controlled amounts from an external source by the external mechanical pumping system described above. Gas can also be delivered from the pressure generated by a standard glass bottle or tank. The fluid or gas delivered to the micro-chambers can be regulated by the micro-valves. The fluid or gas can be used to further alter the crystal growth conditions of the microchamber and increase the size of the protein crystals grown. These protein crystals can then be harvested and examined by x-ray crystallography or nuclear magnetic spectroscopy or other appropriate techniques.

Advantages of the present invention should now be apparent. The present invention provides a method of screening protein crystal growth conditions on a nano or meso scale. The method provides a means of screening protein crystal growth conditions for proteins that cannot be expressed in milligram quantities as well as those that can be expressed in larger quantities. Moreover, the substantial reduction in protein needed for the present invention reduces the costs associated with screening protein crystal growth conditions.

Also provided is an apparatus for screening crystal growth conditions. The apparatus comprises a microarray for the protein and precipitate solutions, an automatic dispensing mechanism for dispensing the solutions and an automated means for analyzing crystal growth.

The desired solutions, i.e., protein, precipitate and a buffer, are preferably automatically dispensed at a preset picoliter or nanoliter volume into the microarray by an automated dispensing mechanism. Preferably, the automatic dispensing mechanism dispenses discrete drops. Screening conditions such as the type of buffer and pH can be varied from sample to sample by programming the automatic dispenser. For example, arbitrary screens varying pH could be programmed by mixing the proper ratios using different drop counts from different stock solutions having different pH values. A pH range from 2.0 to 10.0 is then screened in steps of 0.2-0.5 pH units. Other conditions, such as crystallization agents and salt concentration are also controlled in a similar manner.

Mixing of the reagents can either be done before dispensing or after the solutions are dispensed into the microarray. Mixing in the microarray, for example, can be accomplished by ultrasonic mixing, high-speed dispensing of picoliter drops, rapid temperature fluctuation, or by static diffusion.

After mixing, preferably the wells of the microarray are sealed to control the microenvironment in the wells and to prevent evaporation of the solutions to dryness. More preferably, the wells are sealed with optically clear tape. Sealing the microarray involves an arm mounted on a YZ transverse mechanism. The X direction is along the plate transport direction. The arm, holding a roll of clear tape, moves past the last well in the row, drops to form positive vertical (Z axis) pressure, and then begins to move back in the negative Y direction while at the same time rotating the tape roll. Once the tape leaves the plate area, a guillotine mechanism shears the tape. The plate then moves in the X direction onto the next indexed row and the dispense process initializes again. Automated taping is reliably performed in many industries.

Protein crystal growth in the different wells is monitored by high resolution optical means which automatically detects crystal growth based on well known edge analysis. Such image acquisitions systems are commercially available.

The foregoing and other aspects of the invention may be better understood in connection with the following example, which is presented for purpose of illustration and not by way of limitation.

EXAMPLE 1

Figure 3:
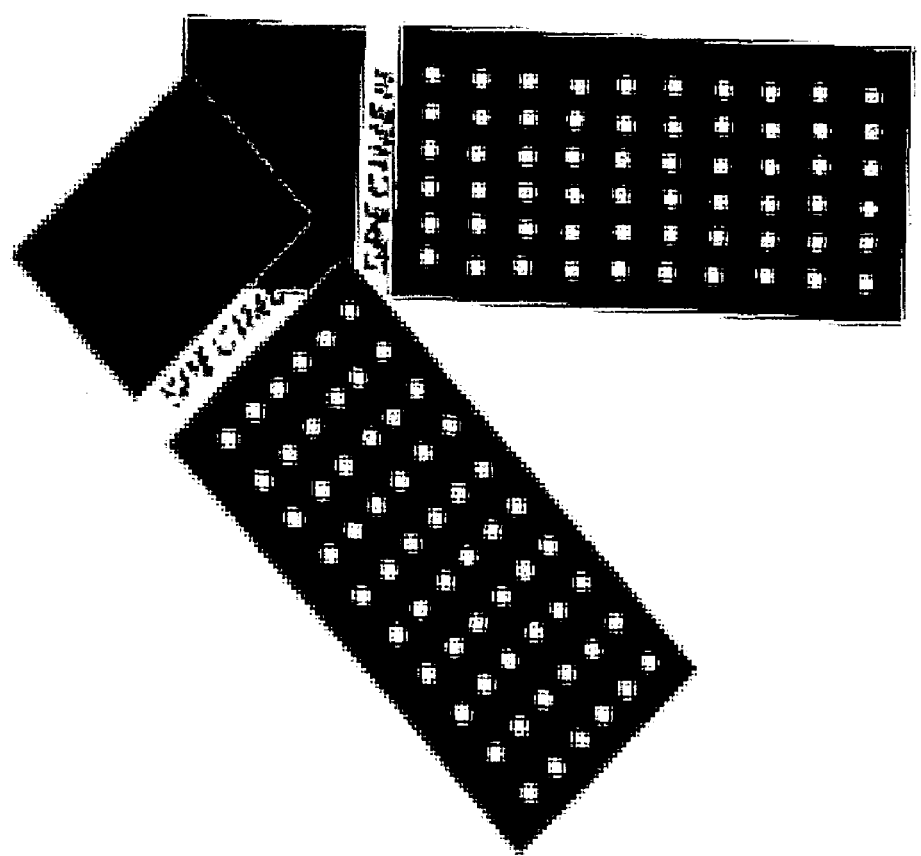
FIG. 3 is a photograph showing a microarray.
Figure 4:
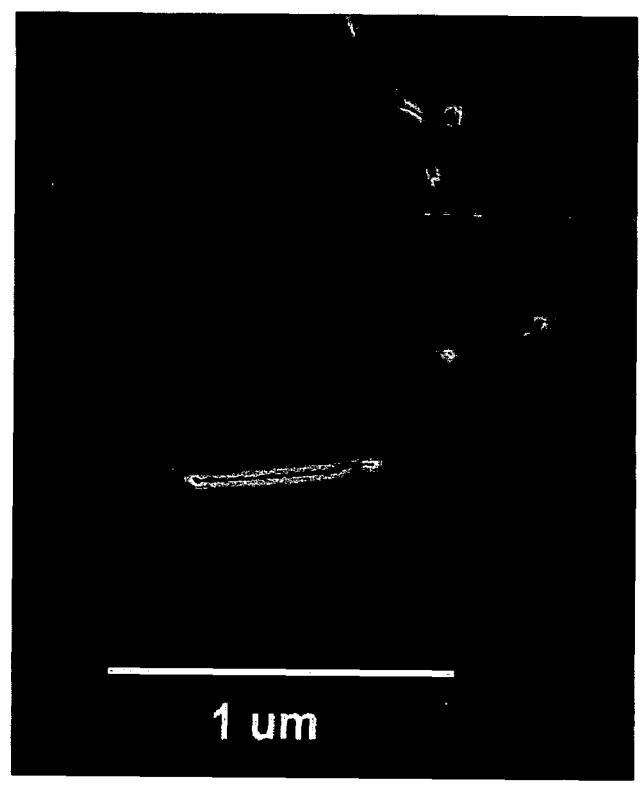
FIG. 4 is a photograph of a protein crystal obtained with nanogram amounts of protein in nanoliter volumes.

Nanoliter protein droplets were used for vapor diffusion, batch and liquid diffusion crystallization screening. The protein solutions of either lysozyme, thaumatin, or NAD synthetase were applied using a five microliter Hamilton syringe. To ensure complete wetting of the small droplet to the experiment chamber, the tip of the Hamilton syringe was placed in contact with the wall of each experiment chamber. A variety of microarrays were designed to accommodate protein solution droplets with volume ranges of 5-20 nanoliters and precipitate volumes of 100-200 nanoliters. The array prototyping was accomplished using MicroScope slides with permanent sealing of neoprene gaskets of varying thickness (0.1 mm 0.5 mm). Once all solutions were applied to an individual experiment chamber within the microscope slide, the experiment was sealed (with oil or grease) by placing a glass cover slide over the top of the gasket. FIG. 3 is a photograph of a typical design for a 60 chamber array prototype (gasket thickness=0.1 mm) and FIG. 4 is a photograph of crystals that were grown to 10 nanoliter protein droplets using a similar microarray slide.

A Cartesian robotic dispensing system was used to prepare crystallization solutions in a 6 by 10 experiment array. Five nanoliters of protein plus five nanoliters of precipitant were dispensed into one merged droplet in one depression in the experiment chamber (FIG. 3) and 50 nanoliters of precipitant plus 50 nanoliters of buffer were merged into one droplet in the connected depression. Thus, four solutions were dispensed for each experiment, and 6×10×4=240 total for the entire 6 by 10 array. Cartesian's instrument was able to dispense all of the solutions in less than 20 minutes. All external conditions used were known crystallization conditions for the particular proteins tested. The experiment was manually sealed and incubated at 22° C. for a period of one day. Crystals were observed in seventy percent of the droplets. While not wishing to be bound by theory, it is believed that the failure to observe crystals in 30% of the wells was due to inaccurate dispensing of the protein and precipitant five nanoliter drops in that the peizo tip did not position the drops together.

From the above description of the invention, those skilled in the art will perceive improvements, changes and modifications. Such improvements, changes and modifications within the skill of the art are intended to be covered by the appended claims.

Having described the invention the following is claimed:

1. A method for determining crystallization conditions for a protein, the method comprising:

delivering material to micro-chambers connected by micro-channels within a micro-array to form a plurality of different crystallization samples, the plurality of different crystallization samples comprising a protein to be crystallized and crystallization conditions which vary among the plurality of different crystallization samples;

allowing crystals of the protein to form in the plurality of crystallization samples within the microfluidic device; and, identifying which of the plurality of crystallization samples within the microfluidic device comprise a precipitate or a crystal of the protein.

2. A method for determining crystallization conditions for a protein, the method comprising:

within a microfluidic device, delivering material to an enclosed microchamber via means for transmitting a fluid to the microchamber from an external source to form a plurality of different crystallization samples, the plurality of different crystallization samples comprising a protein to be crystallized and crystallization conditions which vary among the plurality of different crystallization samples;

allowing crystals of the protein to form in the plurality of crystallization samples within the microfluidic device; and, identifying which of the plurality of crystallization samples within the microfluidic device comprise a precipitate or a crystal of the protein.

* * * * *